(12) United States Patent
Cassaday

(10) Patent No.: US 9,198,523 B2
(45) Date of Patent: Dec. 1, 2015

(54) CHAIR OR BED MEMBER HAVING DATA STORAGE

(76) Inventor: Terry Cassaday, Toronto (CA)

( * ) Notice: Subject to any disclaimer, the term of this patent is extended or adjusted under 35 U.S.C. 154(b) by 2531 days.

(21) Appl. No.: 11/167,082

(22) Filed: Jun. 28, 2005

(65) Prior Publication Data

US 2005/0240108 A1    Oct. 27, 2005

Related U.S. Application Data

(62) Division of application No. 10/374,429, filed on Feb. 27, 2003, now Pat. No. 7,378,978.

(51) Int. Cl.
| | |
|---|---|
| *A61B 5/024* | (2006.01) |
| *A61B 5/021* | (2006.01) |
| *A61B 5/0245* | (2006.01) |
| *A61B 5/02* | (2006.01) |
| *A61G 7/018* | (2006.01) |
| *A47C 1/022* | (2006.01) |
| *B60N 2/02* | (2006.01) |
| *A47C 31/12* | (2006.01) |
| *A61B 5/00* | (2006.01) |

(52) U.S. Cl.
CPC .............. *A47C 31/126* (2013.01); *A47C 1/022* (2013.01); *A61B 5/486* (2013.01); *A61B 5/6887* (2013.01); *A61B 5/021* (2013.01); *A61B 5/024* (2013.01); *A61G 7/018* (2013.01); *B60N 2/0228* (2013.01); *B60N 2/0248* (2013.01); *G05B 2219/36463* (2013.01); *G05B 2219/45022* (2013.01)

(58) Field of Classification Search
CPC ...... A47C 1/022; A47C 31/126; A61B 5/021; A61B 5/024; A61B 5/486; A61B 5/6887; A61G 7/018; B60N 2/0228; B60N 2/0248; B60R 1/025; B60R 1/07; B60R 22/44; G05B 2219/36463; G05B 2219/45022; G05B 2219/45185

USPC ......... 600/481, 483, 485, 500–509, 595, 300, 600/301

See application file for complete search history.

(56) References Cited

U.S. PATENT DOCUMENTS

| | | | | |
|---|---|---|---|---|
| 3,760,794 | A * | 9/1973 | Basham | 600/535 |
| 3,898,981 | A * | 8/1975 | Basham | 600/535 |
| 3,996,922 | A * | 12/1976 | Basham | 600/535 |
| 4,066,072 | A * | 1/1978 | Cummins | 601/15 |
| 4,299,233 | A * | 11/1981 | Lemelson | 600/500 |
| 4,444,199 | A * | 4/1984 | Shafer | 600/504 |
| 4,509,527 | A * | 4/1985 | Fraden | 600/484 |
| 4,595,023 | A * | 6/1986 | Bonnet | 600/595 |
| 4,657,025 | A * | 4/1987 | Orlando | 600/484 |
| 4,665,926 | A * | 5/1987 | Leuner et al. | 600/529 |
| 4,698,571 | A * | 10/1987 | Mizuta et al. | 318/568.1 |
| 5,002,060 | A * | 3/1991 | Nedivi | 600/484 |
| 5,353,012 | A * | 10/1994 | Barham et al. | 340/573.4 |
| 5,435,317 | A * | 7/1995 | McMahon et al. | 600/534 |
| 5,448,996 | A * | 9/1995 | Bellin et al. | 600/574 |
| 5,479,932 | A * | 1/1996 | Higgins et al. | 600/529 |
| 5,479,939 | A * | 1/1996 | Ogino | 600/595 |
| 5,515,865 | A * | 5/1996 | Scanlon | 600/534 |
| 5,590,650 | A * | 1/1997 | Genova | 600/301 |
| 5,683,137 | A * | 11/1997 | McDonald et al. | 297/217.3 |

(Continued)

*Primary Examiner* — Navin Natnithithadha
(74) *Attorney, Agent, or Firm* — Eugene Gierczak

(57) ABSTRACT

A chair or bed member has data storage of information regarding the chair or bed member. The chair or bed member further has a sensor which senses physical movement by a person using the chair or bed member to produce an output of the information from the data storage.

13 Claims, 5 Drawing Sheets

(56) References Cited

U.S. PATENT DOCUMENTS

| | | | |
|---|---|---|---|
| 5,684,460 A * | 11/1997 | Scanlon | 340/573.1 |
| 5,698,571 A * | 12/1997 | Audia et al. | 514/323 |
| 5,724,990 A * | 3/1998 | Ogino | 600/587 |
| 5,853,005 A * | 12/1998 | Scanlon | 600/459 |
| 5,902,255 A * | 5/1999 | Ogino | 600/595 |
| 5,930,152 A * | 7/1999 | Dumont et al. | 700/302 |
| 5,964,720 A * | 10/1999 | Pelz | 600/595 |
| 5,978,976 A * | 11/1999 | Chai | 4/483 |
| 6,047,424 A * | 4/2000 | Osborne et al. | 5/713 |
| 6,048,310 A * | 4/2000 | Yasushi et al. | 600/300 |
| 6,163,903 A * | 12/2000 | Weismiller et al. | 5/610 |
| 6,195,008 B1 * | 2/2001 | Bader | 340/573.1 |
| 6,239,706 B1 * | 5/2001 | Yoshiike et al. | 340/573.4 |
| 6,271,760 B1 * | 8/2001 | Watanabe et al. | 340/667 |
| 6,337,629 B1 * | 1/2002 | Bader | 340/576 |
| 6,375,621 B1 * | 4/2002 | Sullivan | 600/484 |
| 6,425,862 B1 * | 7/2002 | Brown | 600/300 |
| 6,450,957 B1 * | 9/2002 | Yoshimi et al. | 600/309 |
| 6,506,153 B1 * | 1/2003 | Littek et al. | 600/301 |
| 6,543,321 B1 * | 4/2003 | Heider | 82/163 |
| 6,547,743 B2 * | 4/2003 | Brydon | 600/534 |
| 6,560,803 B2 * | 5/2003 | Zur | 5/654 |
| 6,840,907 B1 * | 1/2005 | Brydon | 600/534 |
| 6,852,086 B2 * | 2/2005 | Atlas et al. | 600/595 |
| 6,932,774 B2 * | 8/2005 | Nakatani et al. | 600/534 |
| 7,008,022 B2 * | 3/2006 | Cassaday | 297/463.1 |
| 7,015,818 B2 * | 3/2006 | Takashima | 340/576 |
| 7,048,697 B1 * | 5/2006 | Mitsuru | 600/587 |
| 7,154,397 B2 * | 12/2006 | Zerhusen et al. | 340/573.1 |
| 7,378,978 B2 * | 5/2008 | Cassaday | 340/667 |
| 7,652,581 B2 * | 1/2010 | Gentry et al. | 340/573.1 |
| 7,666,151 B2 * | 2/2010 | Sullivan et al. | 600/587 |
| 8,016,351 B2 * | 9/2011 | Cassaday | 297/217.1 |
| 2002/0044059 A1 * | 4/2002 | Reeder et al. | 340/573.1 |
| 2002/0065470 A1 * | 5/2002 | Cassaday | 600/485 |
| 2003/0052787 A1 * | 3/2003 | Zerhusen et al. | 340/573.1 |
| 2003/0130582 A1 * | 7/2003 | Cassaday | 600/485 |
| 2004/0129478 A1 * | 7/2004 | Breed et al. | 180/273 |
| 2005/0240108 A1 * | 10/2005 | Cassaday | 600/485 |

* cited by examiner

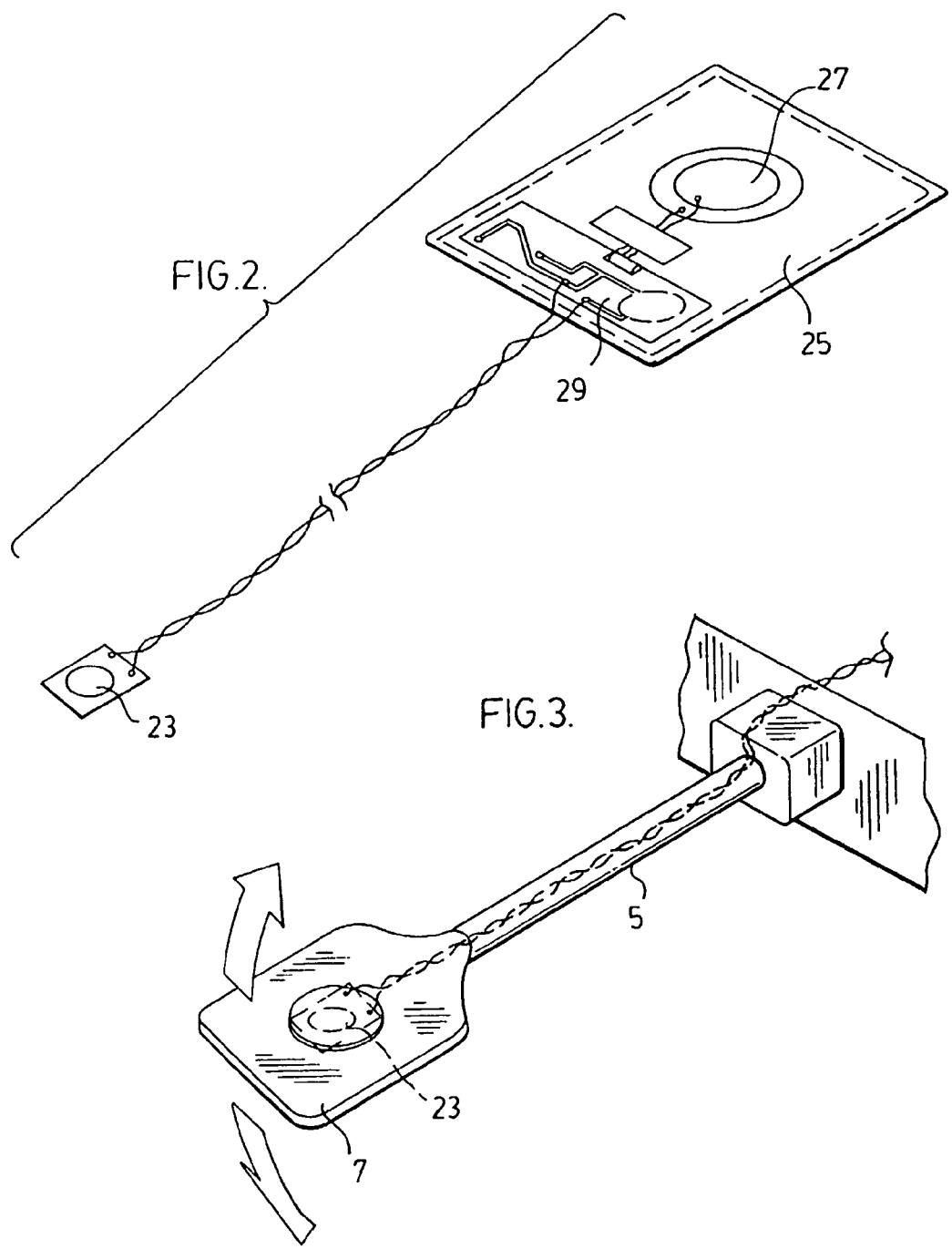

CHAIR OR BED MEMBER HAVING DATA STORAGE

This application is a division of application Ser. No. 10/374,429, filed Feb. 27, 2003 now U.S. Pat. No. 7,378,978.

FIELD OF THE INVENTION

The present invention relates to a chair or bed member having moving parts and controls for those moving parts.

BACKGROUND OF THE INVENTION

A comfortable sitting or lying position for one person may not be comfortable for another person. Furthermore, people come in all different shapes and sizes. Accordingly, essentially all up to date office chairs have numerous different moveable parts to accommodate for different people. Each of these parts typically has its own control.

The same is true of adjustable lounge chairs and even for some of the newly designed adjustable beds.

When a person purchases anyone of the above items, the item will come with some type of manual describing proper use of the item. At this point, there is generally no concern that the person using the chair or bed member will not know how to set the proper positions for the different moveable parts.

There are however times when set up operation is not as apparent. For example, when a second person wishes to use the chair or bed or even when the person who set it up has not used the chair or bed for an extended period of time the operation of the controls can become confusing.

There are also times where one wishes to re-order a product such as for example, an office chair or the like without being able to immediately lay his/her hands on the required information for re-ordering purposes.

SUMMARY OF THE PRESENT INVENTION

The present invention relates to a chair or bed member which overcomes the drawbacks noted above. More particularly, the chair or bed member of the present invention is one which has data storage means containing information regarding the chair or bed member and further has a physical movement sensing means which produces an output of the information from the data storage means.

According to an aspect of the invention the data storage means comprises a computer chip and the physical movement sensing means comprises a pressure sensor to produce the output from the computer chip. This output can be either audible or visual.

According to another aspect of the invention the chair or bed member has different moveable parts with controls for those parts. The data storage means contains information as to how to use the controls.

According to another aspect of the invention the data storage means contains information as to the history of the chair or bed member which can be used for example, for re-ordering purposes.

BRIEF DESCRIPTION OF THE DRAWINGS

The above as well as other advantages and features of the present invention will be described in greater detail according to the preferred embodiments of the present invention in which;

FIG. 2 is perspective view looking down on a sensor and information containing system from the chair of FIG. 1.

FIG. 3 is a perspective view showing the mounting of the sensor in the chair of FIG. 1.

DETAILED DESCRIPTION ACCORDING TO THE PREFERRED EMBODIMENTS OF THE PRESENT INVENTION IN WHICH

Figure 1:
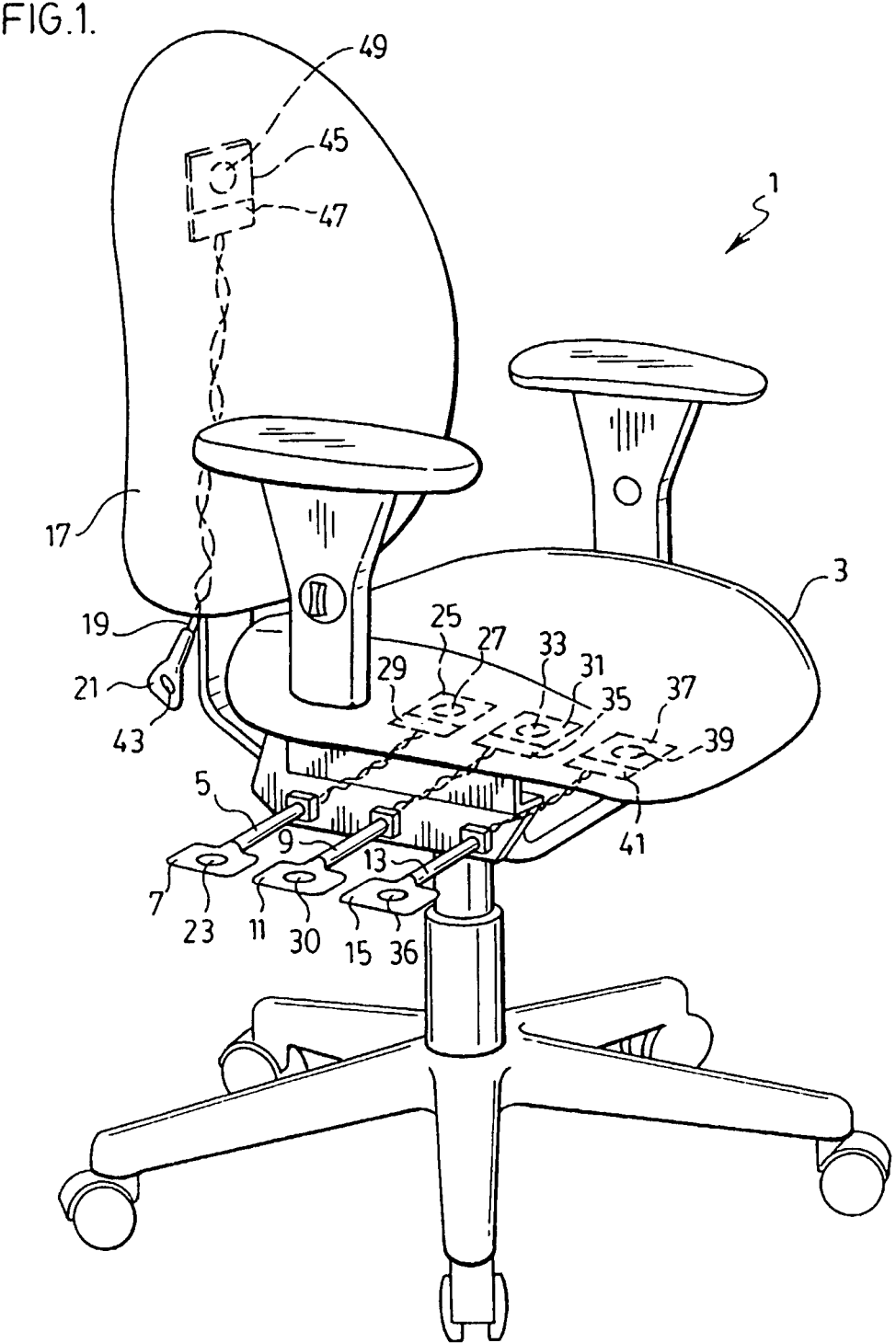
FIG. 1 is a perspective view of an office chair made in accordance with a preferred embodiment of the present invention.

FIG. 1 shows an office type chair generally indicated at 1. This chair has a chair seat 3 and a chair back 17. Both the seat and the back of the chair are moveable to different positions of use of the chair. These different portions allow the person using the chair to assume different ergonomically desirable body positions when seated in the chair.

More particularly, seat 3 is adjusted by means of lever controls 5, 9 and 13. Each of these lever controls includes a control paddle 7, 11 and 15 respectively.

The chair back is adjustable by means of a lever 19 having a control paddle 21.

Each of the above lever controls, with associated paddle, controls a different adjustment such as for example, height or angle adjustment for the chair seat and angle adjustment for the chair back. The actual manner of making the adjustment through the appropriate control is typically something that is learned by the initial user of the chair during set-up but not necessarily known to a second user of the chair or possibly forgotten over time by the initial user of the chair.

In accordance with the present invention the chair itself includes operating instructions for the control.

More particularly, the chair includes its own data storage means and a physical movement sensor to produce an output from the data storage means. In the preferred embodiment shown the data storage means comprises pre-programmed computer chips with pressure sensors for producing an output from the computer chips.

In chair 1 a plurality of chip boards 25, 31 and 37 are mounted to the underside of the chair seat. Pressure sensors 23, 30 and 36 wired to the respective chip boards are located within the paddles 7, 11 and 15 as shown in FIG. 1.

The chip boards 25, 31 and 37 further include small speakers 27, 33 and 39.

A further chip board 45 carrying a pre-programmed computer chip 47 and a speaker 49 is mounted to the rear of the chair back. A pressure sensor 43 located in paddle 21 is wired to chip board 45.

With the user sitting in the chair he or she can press on any one of the pressure sensors and the associated computer chip will then provide an audible output as to operation of the lever in which the pressure sensor is mounted. This eliminates any guess work in how to set the chair up properly.

It is to be understood that if the chair user does not need directions the controls can be manipulated without having to push on any of the pressure sensors.

It is also to be appreciated that other types of physical movements sensors such as heat or light sensors could be used in the controls. When the person moves his or her hands close to or over these types of sensors they will also produce an output from the programmed chips.

FIG. 2 shows in more detail pressure sensor 23 wired to chip board 25 carrying programmed chip 29 and speaker 27. FIG. 3 shows how the wiring between the pressure sensor and the chip board fits through the hollow interior of the lever 5 from the lever paddle 7 to the chair base. Accordingly, the levers provide a protective covering for what would otherwise be open, unsightly wiring on the chair.

Figure 4:
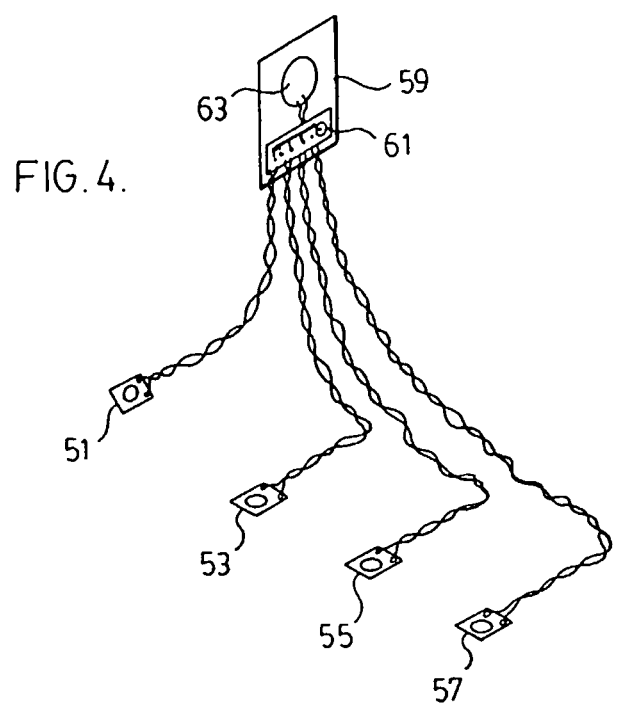
FIGS. 4 through 6 show a different sensing and data storage set-ups according to different preferred embodiments of the present invention.

In lieu of using a plurality of separate chips and chip boards, FIG. 4 demonstrates that a plurality of sensors 51, 53, 55 and 57 can all be hooked into one board 59 containing a single chip 61 programmed with information regarding all of the controls. The pressure sensors themselves would once again be located at the individual control paddles. A single speaker 63 would provide the audible output of the chair operation information.

Figure 5:
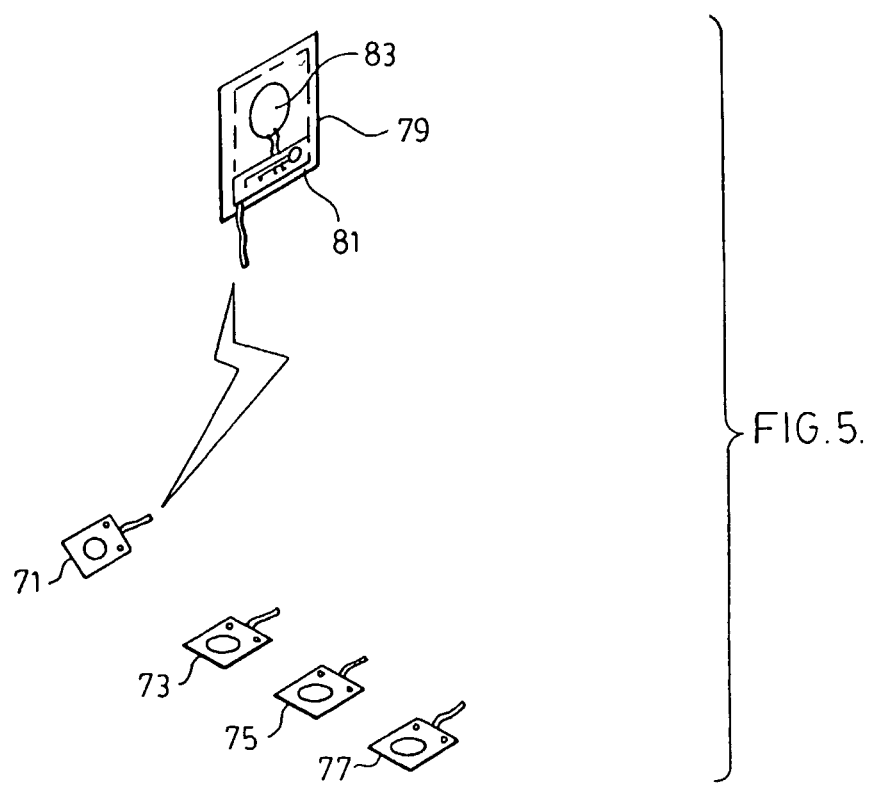

FIG. 5 demonstrates a principal similar to FIG. 4 with the exception that a plurality of sensors generate airborne rather than hard wire signals to a chip board 79 carrying a computer chip 81 and a speaker 83 for outputting from chip 81.

All of the description above relates to an audible output from the computer chip data storage in the chair. However, it is to be easily understood from FIG. 5 that anyone of the sensors 71 through 77 could generate signals for a video output by means of a display screen which could be either on board or remote of the chair. A particularly good system is one in which the output is visually displayed on a computer monitor which is operated from the chair.

Figure 6:
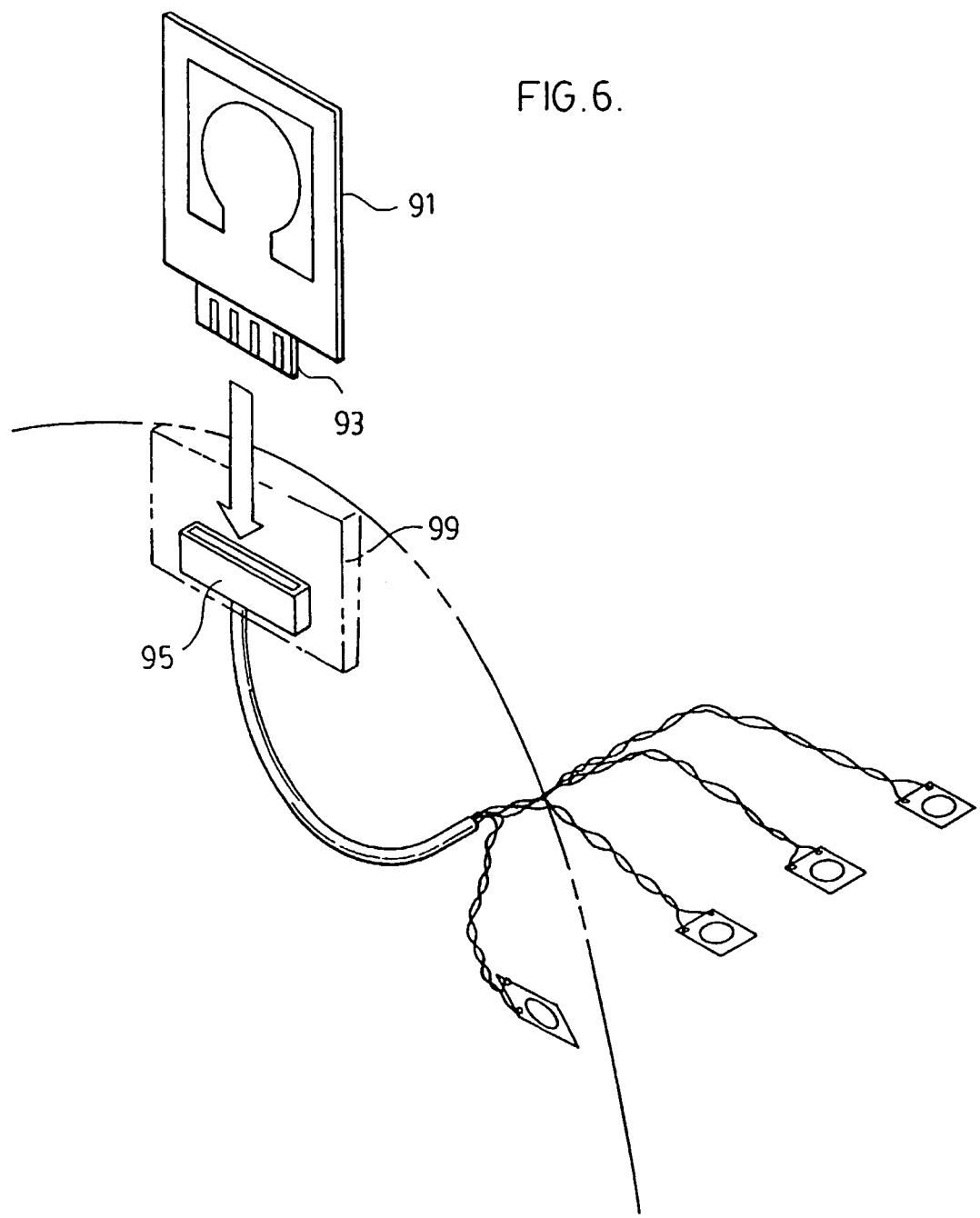

Over time the small battery carried by the chip board for its operation will eventually fail. FIG. 6 of the drawings shows a replaceable chip board 91 having a male contact end 93 which plugs into a socket 95 wired back to a plurality of sensors shown in FIG. 6. This chip board, once its life has expired, can easily be replaced by a new chip board.

Note that in FIG. 6, chip board 91 seats within a pocket 99 located high on the back of the chair. Pocket 99 acts to effectively hide the chip board, is in a location almost level with the head of the chair user so that the user can easily hear the instructions from the small speaker on the chip board.

In the description above, reference is made to each of the controls including directions as to how to use the controls. According to a further aspect of the invention the information carried in any one or all of the chips can be history information regarding the chair. For example, any one of the chips can identify serial number, the manufacturer or even the construction of the chair. This allows for easy re-ordering of the chair.

Figure 7:
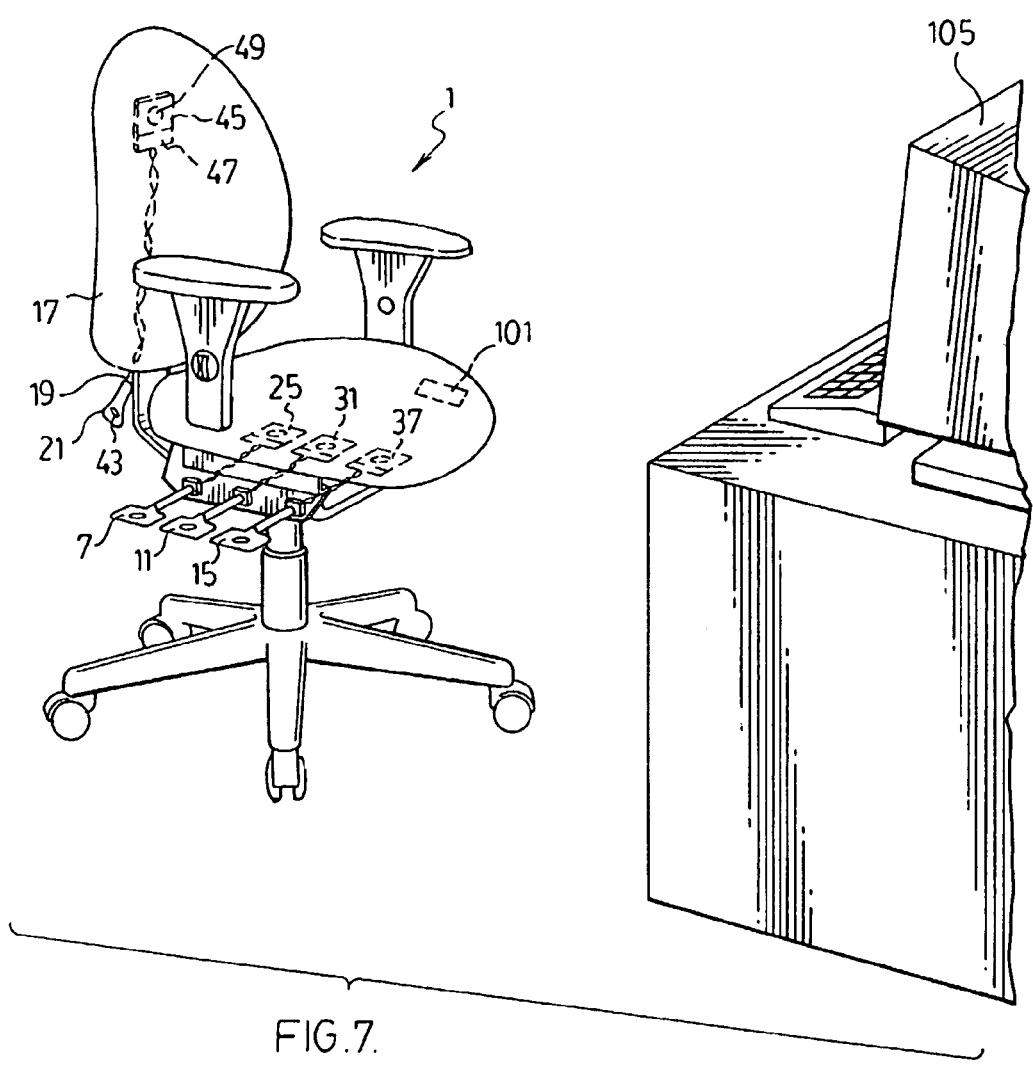
FIG. 7 shows an office chair incorporating further features according to still another embodiment of the invention.

FIG. 7 shows another embodiment of the invention in which the chair includes an additional sensor 101. This sensor is buried slightly below the surface of the seat of the chair, it is located in the area such that it would be directly below the back of the thigh of a person sitting in the chair. It can equally as well be buried in the armrest of the chair where a person would place his or her forearm. These are two areas of the body from which a person's biorhythms indicating things such as heart rate, blood pressure, etc. can be felt. The sensor picks up these biorhythms and they are then output from the sensor.

In the set shown in FIG. 7, the chair is used to seat a person to use of computer 105. This computer is programmed to accept and display the output from sensor 101. In this way the person using the chair can easily obtain a medical check-up by simply sitting in the chair.

If the person does not want such information every time he or she sits in the chair the bio feedback system can simply be turned off at the computer.

It is to be further understood that although the description is specific to an office chair the concept of the invention equally applies to any type of a chair, lounge or bed having moving parts. Accordingly, although various preferred embodiments of the present invention have been described, it is to be appreciated that variations may be made without departing from the spirit of the invention or the scope of the appended claims.

I claim:

1. An apparatus comprising: a chair, lounge or bed member; and a display unit to provide a biorhythm signal of a person when a person occupies said chair, lounge or bed member;
    said chair lounge or bed member including moveable parts and one or more levers which enable movement of said moveable parts;
    a sensor disposed in said chair, lounge or bed member for receiving and transmitting a biorhythm signal of said person occupying said chair, lounge or bed member; and
    a processing unit associated with said display unit for selectively:
        (i) activating said display unit to display said biorhythm signal of said person;
        (ii) deactivating said display unit; and
    a data storage device containing instructional information regarding operating functions of said one or more levers, each said one or more levers having a switch which when activated produce an output of the instructional information without producing operation of said moveable parts.

2. An apparatus as claimed in claim 1, wherein said display unit comprises a computer remotely disposed in front of said chair, lounge or bed member, said computer including a display.

3. An apparatus as claimed in claim 2 wherein said computer is used to deactivate said display.

4. An apparatus as claimed in claim 2 wherein said computer is used to deactivate said sensor.

5. An apparatus as claimed in claim 1 wherein said display unit comprises a display disposed on the armrest of said chair.

6. An apparatus as claimed in claim 1 wherein said one or more levers can be activated to move said moveable parts to assume different ergonomically desirable body positions when occupying said chair, lounge or bed member.

7. An apparatus as claimed in claim 6 wherein both said instructional information and said biorhythm signal of a person is displayed on said display unit.

8. An apparatus as claimed in claim 7 wherein said computer is programmed to accept and display both said instructional information and said biorhythm signal of a person.

9. An apparatus as claimed in claim 1 further comprising an audible output device for outputting said instructional information.

10. An apparatus as claimed in claim 9 wherein said audible output device is one or more speakers.

11. An apparatus as claimed in claim 1 wherein said data storage device further contains history information for the chair, lounge, or bed member.

12. A chair or bed member comprising:
    a moveable part and a lever which enables movement of said moveable part;
    a sensor for sensing biorhythm signal of a person in said chair or bed member and transmitting said biorhythm signal to a display unit to display the person's biorhythm each time the person occupies the chair or bed member; and
    a data storage device for storing both instructional and operational information regarding the moveable part and;

said lever having a switch, said switch when activated displays the instructional and operational information on said display unit without producing operation of said moveable part.

13. A chair for providing biorhythm information by occupying the chair comprising:
 a) a moveable part;
 b) a sensor disposed in said chair for receiving a biorhythm signal of a person in said chair and transmitting said biorhythm information to a computer display unit to display said biorhythm information of said person;
 c) a data storage device for storing both instructional and operational information regarding the moveable part and;
 d) a lever for moving said moveable part, the lever having a switch, where said switch when activated displays the instructional and operational information on said computer display unit, without producing movement of said moveable part.

* * * * *